(12) United States Patent
Chacon et al.

(10) Patent No.: US 6,255,128 B1
(45) Date of Patent: Jul. 3, 2001

(54) NON-CONTACT METHOD FOR DETERMINING THE PRESENCE OF A CONTAMINANT IN A SEMICONDUCTOR DEVICE

(75) Inventors: Carlos M. Chacon; Pradip K. Roy, both of Orlando, FL (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/130,240

(22) Filed: Aug. 6, 1998

(51) Int. Cl.[7] .................................................. B01R 31/26
(52) U.S. Cl. ................................. 438/17; 438/14; 324/455
(58) Field of Search ................................. 438/14, 17, 18; 324/452, 455, 753

(56) References Cited

U.S. PATENT DOCUMENTS

| | | | |
|---|---|---|---|
| 4,812,756 | * | 3/1989 | Curtis et al. ........................... 324/750 |
| 5,216,362 | * | 6/1993 | Verkuil ................................. 324/767 |
| 6,011,404 | * | 1/2000 | Ma et al. .............................. 324/765 |

OTHER PUBLICATIONS

O'Mara et al, Handbook of Semiconductor Silicon Technology, 1990, Noyes Publications, New York, reprint edition, p599–635.*

Cosway et al, Manufacturing Implementation of Corona Oxide Silicon (COS) Systems for Diffusion Furnace Contamination Monitoring, 1997, IEEE/SEMI Adv. Semi. Mfg. Conf., pp. 98–102.*

Schroder et al, Corona–Oxide Semiconductor Device Characterization, 1998, Solid State Electronics vol. 42, No. 4, pp. 505–512.*

* cited by examiner

Primary Examiner—Stephen D. Meier
Assistant Examiner—Jeff Vockrodt

(57) ABSTRACT

The present invention provides a non-contact method for determining whether a contaminant is present in a semiconductor wafer having a substrate/dielectric interface formed thereon. in one advantageous embodiment, the method comprises field inducing a junction in equilibrium inversion in the semiconductor wafer device. A conventional corona source may be used to induce the junction to equilibrium inversion. This particular embodiment further includes forming a contaminant junction near the substrate/dielectric interface when the contaminant is present in the semiconductor wafer by adding charge and pulsing the junction out of equilibrium. A surface voltage measurement, which may be taken with a Kelvin probe, is obtained by measuring a change in a surface voltage as a function of time. The method further includes determining whether the contaminant is present in the semiconductor wafer from the change in the surface voltage. When the contaminant is present in the device, the change in the surface voltage is negligible. This negligible change is in stark contrast to the change in surface voltage that occurs in a non-contaminated device. The data obtained from these surface voltages can be plotted with conventional devices to yield the change in surface voltage with respect to time.

14 Claims, 2 Drawing Sheets

NON-CONTACT METHOD FOR DETERMINING THE PRESENCE OF A CONTAMINANT IN A SEMICONDUCTOR DEVICE

TECHNICAL FIELD OF THE INVENTION

The present invention is directed, in general, to a non-contact method for determining the presence of a contaminant in a semiconductor device and, more specifically, to a non-contact method for determining donor atom contamination in a p-type silicon and acceptor atom contamination in an n-type silicon.

BACKGROUND OF THE INVENTION

The ongoing trends toward larger wafers, shrinking line widths, and ever thinner oxides are making tight in-line monitoring of wafer cleanliness and uniformity even more critical to semiconductor manufacturers. Contaminants can be any form of matter that causes unintentional changes in electrical properties of semiconductor devices. Some common contaminants include particles, atomic-ionic-molecular defects, and heavy metals.

The fabrication of complimentary metal oxide semiconductor (CMOS) devices involves numerous distinct manufacturing process steps. Device contamination, during any of these processes, poses a serious quality control problem and when severe, may necessitate that the devices be scrapped. To monitor contamination that occurs during the manufacturing process, manufacturers have developed tests that attempt to monitor contamination in the semiconductor device.

A measurement of electrically active contamination may be accomplished using a resistivity test. This is often done through the use of a tool having four probes that actually touch the top of the semiconductor wafer, where the tool measures the resistivity between the probes. These measurement probes themselves, however, tend to become contaminated from their contact with the surface and may therefore distort the measurements. Additionally, sensitivity also may be a problem, since electrically active contamination concentrations well below the resistivity measurement capability of the tool can cause performance degradation in the device under test.

Another popular method of measuring the free charges in the semiconductor device is the use of secondary ion mass spectroscopy (SIMS). The SIMS technique bombards the surface of the device under test with high energy charged particles in a "sputtering" fashion. These ions penetrate into the device, to a depth that is a function of their energy level, and excite a secondary ion emission from the device that is proportional to a contamination concentration level. The SIMS then measures the type and concentration of this free charge contamination. However, SIMS suffers from the severe limitation in that it measures concentration levels down to only about 5.0E14 atoms/ml for phosphorous (n-type). Therefore, contaminant concentrations below this level in semiconductor devices are not detected and may still cause serious performance problems. Additionally, the time required for the SIMS measurement process is a function of the target concentration level and may take days to determine the lower levels of contamination.

In summary, these measurement techniques typically require long periods of time to apply and do not have the measurement sensitivity to detect low contaminant concentration levels. Therefore, the information obtained from these tests is not available or detectable at the desired time during the fabrication process. This generally forces the testing to be done after the device has been fully fabricated and the majority of the manufacturing costs have been incurred. Moreover, it is not assured that trace amounts of contaminants will be detected. Additionally, since testing is performed on completed devices, as contrasted with devices that are still in the fabrication process, it is often difficult to determine the exact source or location of the contamination.

Accordingly, what is needed in the art is a way to quickly measure low levels of electrically active contaminants within the semiconductor device.

SUMMARY OF THE INVENTION

To address the above-discussed deficiencies of the prior art, the present invention provides a non-contact method for determining whether a contaminant is present in a semiconductor wafer having a substrate/dielectric interface formed thereon. In one advantageous embodiment, the method comprises field inducing a junction in equilibrium inversion in the semiconductor wafer device. A conventional corona source may be used to induce the junction to equilibrium inversion. This particular embodiment further includes forming a contaminant junction near the substrate/dielectric interface when the contaminant is present in the semiconductor wafer by adding charge and pulsing the junction out of equilibrium. A surface voltage measurement, which may be taken with a Kelvin probe, is obtained by measuring a change in a surface voltage as a function of time. The method further includes determining whether the contaminant is present in the semiconductor wafer from the change in the surface voltage. When the contaminant is present in the device, the change in the surface voltage is insubstantial. This insubstantial change is in stark contrast to the change in surface voltage that occurs in a non-contaminated device. The data obtained from these surface voltages can be plotted with conventional devices to yield the change in surface voltage with respect to time.

Thus, one aspect oft the present invention provides a non-contact method for easily determining whether a contaminant is present in the device early in the semiconductor devices formation. Additionally, the present invention also provides a method that can D readily detect low levels of contamination that has been previously undetectable. Due to the sensitivity and accuracy of this method and the ease with which it can be conducted, substantial fabrication downtime, which is prevalent in present measuring processes, can be saved, thereby lowering the fabrication costs of the semiconductor device. Furthermore, the present method can be used to more closely monitor the cleanliness of the furnaces, which are often a source of contaminates in the semiconductor manufacturing process.

In another embodiment, the formation of the contaminant junction inhibits a formation of a deep depletion region within the semiconductor device. It is believed that the contaminant forms (contaminant skin, which in turn forms a pn junction at or near the substrate/dielectric interface because of the readily available source of either electrons or positive charge associated with the contaminant. The type of pn junction that forms depends on the type of contaminant that is present in the semiconductor device. Most often, the contaminant is a dopant material that is opposite to the dopant with which the device is doped. For example, if the intended dopant is a p-type of dopant, such as Boron, then the contaminant may be an n-type of dopant, such as phosphorous. In such instances, an n-type contaminant junction is formed. Alternatively, the intended dopant may be an n-type dopant and the contaminant dopant may be a p-type dopant, which would form a p-type of contaminant junction. It is believed that the formation of this pn junction prevents deep depletion from occurring in the device.

The foregoing has outlined, rather broadly, preferred and alternative features of the present invention so that those who are stilled in the art may better understand the detailed description of the invention that follows. Additional features of the invention will be described hereinafter that form the subject of the claims of the invention. Those who are skilled in the art should appreciate that they can readily use the disclosed conception and specific embodiment as a basis for designing or modifying other structures for carrying out the same purposes of the present invention. Those who are skilled in the art should also realize that such equivalent constructions do not depart from the spirit and scope of the invention in its broadest form.

BRIEF DESCRIPTION OF THE DRAWINGS

For a more complete understanding of the present invention, reference is now made to the following descriptions taken in conjunction with the accompanying drawings, in which.

DETAILED DESCRIPTION

Figure 1:
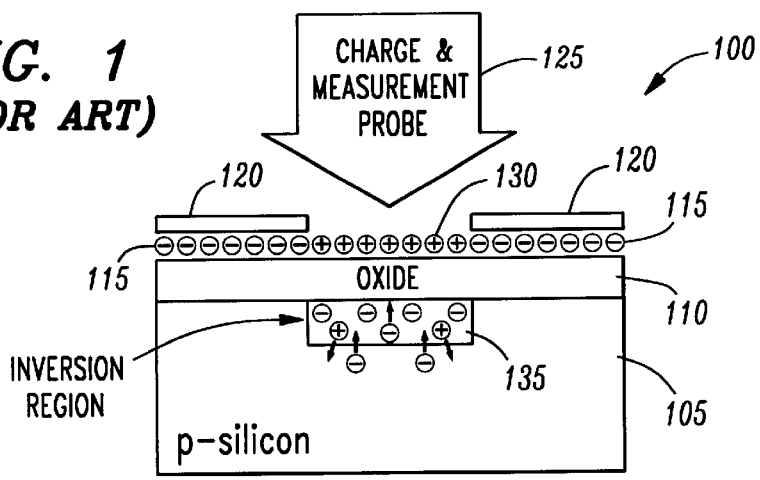
FIG. 1 illustrates a conventional non-contact method that may be used to determine electrical properties of a semiconductor device.

Referring initially to FIG. 1, illustrated is a conventional non-contact method that may be used to determine electrical properties of a semiconductor device 100. The semiconductor device 100 includes a p-silicon substrate 105, an oxide layer 110, a collection of oxide surface charges 115, an isolation mask 120, a charge and measurement probe 125 and an inversion region 135.

The conventional non-contact method employs a conventional Corona Oxide Semiconductor (COS) wafer testing technique. Using this method, a layer of negatively charged particles is initially formed on the exposed top surface of the oxide layer 110. This negatively charged layer brings the p-silicon substrate into a state of p-type carrier accumulation beneath the oxide dielectric layer 110 (not shown).

Then a guard ring 120, which acts as an is isolation mask is positioned to allow only a portion of the surface of the oxide layer 110 to be exposed, through a window in the isolation mask 120, to the charge and measurement probe 125. The charge portion of the charge and measurement probe 125 is used to deposit a layer of positive charges onto the surface portion of the oxide layer 110 that is within the opening of the isolation mask 120, as shown. The positive charges in the charge layer 115 bring the p-silicon substrate into inversion beneath the positively charged surface region of the oxide layer 110 forming the inversion region 135. The inversion layer 135 attracts n-type carriers and repels p-typo carriers.

Figure 2:
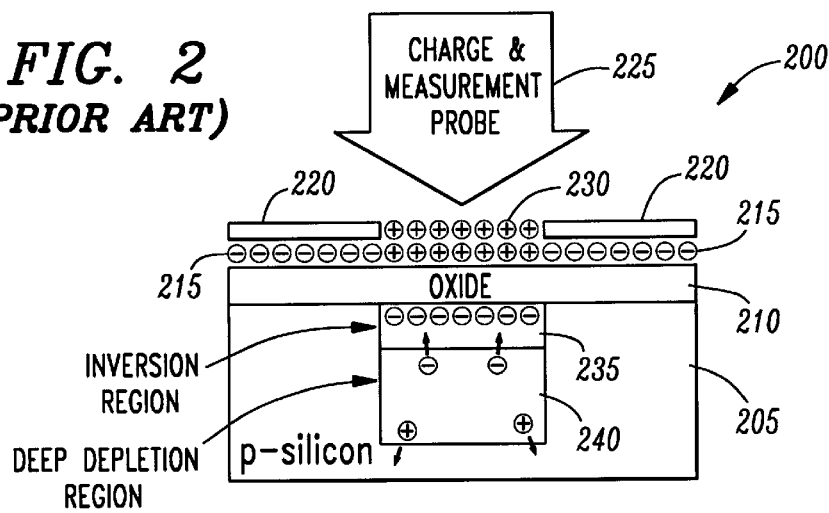
FIG. 2 illustrates an application of the conventional non-contact method of FIG. 1 that may be used to determine electrical properties of a semiconductor device that contains insignificant amounts of electrically active contamination.

Turning now to FIG. 2, illustrated is an application of the conventional non-contact method of FIG. 1 that may be used to determine electrical properties of a semiconductor device 200 that contains insignificant amounts of electrically active contamination. The semiconductor device 200 includes a p-silicon substrate 205, an oxide layer 210, a collection of oxide surface charges 215, an isolation mask 220, a charge and measurement probe 225, an inversion region 235 and a deep depletion region 240.

After establishing the above-discussed initial conditions, the charge and measurement probe 225 adds an additional level of positive charges to the collection of oxide surface charges 215 on the oxide layer 210 through the open area of the guard ring 220. The level of these additional positive charges is sufficient to drive the p-silicon substrate into deep depletion, which creates the deep depletion region 240 that is relatively devoid of p-type carriers. This deep depletion region 240 forms quickly, which is usually within approximately one second. After about two seconds, the charge and measurement probe 225 pulses light through the opening in the isolation mask 220 thereby bombarding the area with photons that causes the deep depletion region 240 to collapse. Measurements are made by the charge and measurement probe 225 when the deep depletion region 240 both forms and collapses.

Figure 3:
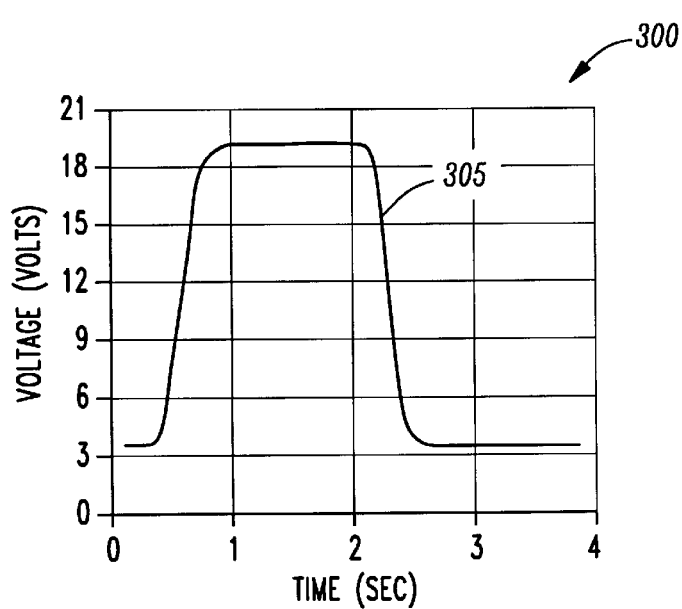
FIG. 3 illustrates a graph showing a waveform that demonstrates a measurement obtained by the method of FIG. 2.

Turning now to FIG. 3, illustrated is a graph 300 showing a waveform 305 that demonstrates a measurement obtained by the method of FIG. 2. The waveform 305 is created in response to the formation and collapse of the deep depletion region 240 as described in FIG. 2. The leading edge of the voltage waveform 305 occurs when the deep depletion region 240 is formed. The trailing edge of the voltage waveform 305 occurs when the deep depletion region 240 collapses.

Figure 4:
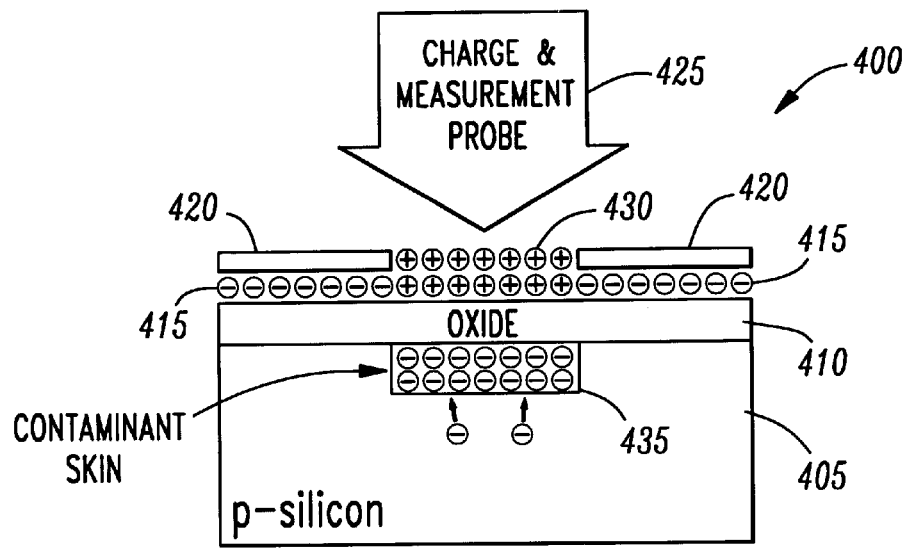
FIG. 4 illustrates an application of a non-contact method that may be used to determine electrical properties of a semiconductor wafer device that contains significant amounts of electrically active contamination.

Turning now to FIG. 4, illustrated is an application of a non-contact method that may be used to determine electrical properties of a semiconductor wafer device 400 that contains significant amounts of electrically active contamination. In this particular embodiment, the semiconductor wafer device 400 includes a p-silicon substrate 405, an oxide layer 410, a collection of oxide surface charges 415, an guard ring 420, a charge and measurement probe 425 and a contaminant junction region 435.

The present invention provides a non-contact method for determining whether a contaminant is present in the semiconductor water device 400 having a substrate/dielectric interface formed by the p-silicon substrate 405 and the oxide layer 410. In this embodiment, the method comprises field inducing a junction that is in equilibrium inversion in the semiconductor wafer device 400. A conventional corona source, which is part of the charge and measurement probe 425, may be used tc) initially induce the junction to equilibrium inversion. This particular embodiment further includes forming the contaminant junction 435 near the substrate/dielectric interface when the contaminant is present in the semiconductor wafer by adding charge and pulsing the junction out of equilibrium.

A surface voltage measurement, which may be taken with a Kelvin probe as part of the charge and measurement probe 425, is obtained by measuring a change in a surface voltage as a function of time. The change in the surface voltage is insubstantial when the contaminant is present in the device, which is in stark contrast to the change in surface voltage that occurs in a non-contaminated device as will be shown in FIG. 5. The data obtained from these surface voltages may be easily plotted with conventional devices to yield the change in surface voltage with respect to time.

The formation of the contaminant junction inhibits formation of a deep depletion region within the semiconductor device 400. It is believed that the contaminant forms a skin, which in turns allows the formation of a pn junction at or near the substrate/dielectric interface 405, 410, shown as the contaminant junction region 435, because of the readily available source of the electrically active contaminants.

The type of pn junction that forms depends on the type of contaminant that is present in the semiconductor device 400. Most often, the contaminant is a dopant material that is opposite to the dopant required by the device. If a p-type dopant is intended as shown in the P-silicon substrate 405, such as Boron, the contaminant may be an n-type off dopant, such as phosphorous. This contaminant forms a pn junction across the oxide layer 410, where the n-type contaminant collects in the contaminant junction region 435 as shown. Alternatively, if the intended dopant is an n-type, the contaminant dopant may be a p-type dopant. This would form a p-type of contaminant in the contaminant junction region 435, since the charges formed by the corona source of the charge and measurement probe 425 would be of negative polarity in the window of the isolation mask 420 on the surface of the oxide layer 410. Additionally, other combinations of electrically active contaminants but should be detectable using this method.

A distinct advantage provided by the present invention is the method's enhanced sensitivity to low concentration levels of contaminants, which is at least an order of magnitude more sensitive than conventional methods. For example, as previously mentioned, the SIMS method provides for contaminant detection only to a level of about 5.0E14. In contrast, the method of the present invention may provide contaminant sensitivity to a level of about 1.0E9 or below. Therefore, the present invention can be used to detect contaminant levels that have previously been undetectable, and semiconductor devices can be rejected based on detection of these contaminants.

Figure 5:
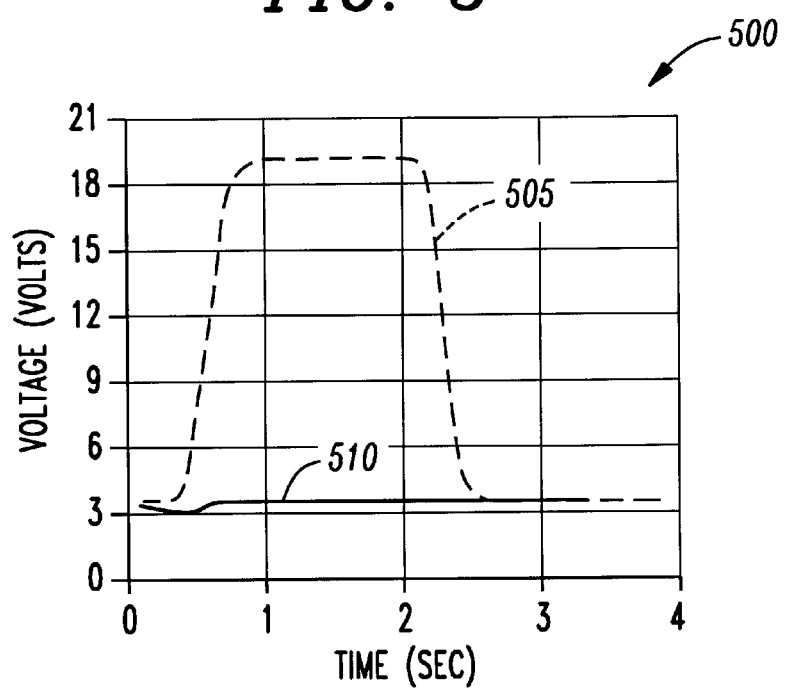
FIG. 5 illustrates a graph showing a waveform that illustrates the measurements obtained by the method of FIG. 4.

Turning now to FIG. 5, illustrated is a graph 500 showing a waveform 510 that illustrates the measurements obtained by the method of FIG. 4. The graph 500 includes the waveform 505, which occurs for the case an insufficient amount of electrically active contaminant, and the waveform 510, which reflects a condition of significant amounts of electrically active contamination.

The waveform 510 is the result of a surface voltage measurement, which may be taken with a Kelvin probe as part of the charge and measurement probe 425, as discussed in FIG. 4. The charge in the surface voltage, as seen in waveform 510, is insubstantial when the contaminant is present in the device. This is seen to be in stark contrast to the change in surface voltage that occurs in a non-contaminated device, which is shown in waveform 505 for comparison. This dramatic visual difference in these graphs provided an excellent tool for readily determining when contamination is present in the semiconductor device.

Although the present invention has been described in detail, those who are skilled in the art should understand that they can make various changes, substitutions and alterations herein without departing from the spirit and scope of the invention in its broadest form.

What is claimed is:

1. A non-contact method for determining whether a contaminant is present in a semiconductor wafer having a substrate/dielectric interface formed thereon, comprising:

field inducing a first junction in equilibrium inversion in said semiconductor wafer device;

forming a contaminant junction near said substrate/dielectric interface when said contaminant is present in said semiconductor wafer by adding charge and poising said first junction out of equilibrium;

measuring a change in a surface voltage as a function of time to obtain a surface voltage measurement, said change being negligible when said contaminant is present in said semiconductor wafer; and determining whether said contaminant is present in said semiconductor wafer from said change in said surface voltage.

2. The method as recited in claim 1 wherein said formation of said contaminant junction inhibits a formation of a deep depletion region within said semiconductor device.

3. The method as recited in claim 1 wherein said semiconductor device comprises a p-type dopant and said contaminant is an n-type dopant.

4. The method as recited in claim 1 wherein said semiconductor device comprises an n-type dopant and said contaminant is a p-type dopant.

5. The method as recited in claim 1 wherein said pulsing is performed with a corona source.

6. The method as recited in claim 1 wherein said measuring is performed with a Kelvin probe.

7. The method as recited in claim 1 wherein said contaminant junction is a p-type junction or an n-type junction.

8. A process for fabricating a semiconductor device, comprising;

forming a substrate/dielectric interface on a semiconductor wafer substrate by growing a dielectric on said semiconductor wafer substrate;

using a non-contact method to determine whether a contaminant is present in said semiconductor device, including:

field inducing a first junction in equilibrium inversion in said semiconductor wafer substrate;

adding charge and pulsing said first junction out of equilibrium, said pulsing forming a contaminant junction near said substrate/dielectric interface when said contaminant is present in said semiconductor device;

measuring a change in a surface voltage as a function of time to obtain a surface voltage measurement, said change being negligible when said contaminant is present in said semiconductor device; and determining whether said contaminant is present in said semiconductor device from said change in said surface voltage; and rejecting said semiconductor device if contaminant is present or continuing said fabrication if said contaminant is not present in said semiconductor device.

9. The process as recited in claim 8 wherein said formation of said contaminant junction inhibits a formation of a deep depletion region within said semiconductor device.

10. The process as recited in claim 8 wherein said semiconductor device comprises a p-type dopant and said contaminant is an n-type dopant.

11. The process as recited in claim 8 wherein said semiconductor device comprises an n-type dopant and said contaminant is a p-type dopant.

12. The process as recited in claim 8 wherein said pulsing is performed with a corona source.

13. The process as recited in claim 8 wherein said measuring is performed with a Kelvin probe.

14. The process as recited in claim 8 wherein continuing said fabrication includes:

forming an active region on said semiconductor substrate, said active region comprising a gate formed on said semiconductor substrate, source and drain regions formed within said semiconductor substrate, a dielectric formed over said gate and source and drain regions, contact openings formed within said dielectric and interconnect structures formed on said dielectric to connect said active region to other portions of the semiconductor wafer.

\* \* \* \* \*